United States Patent [19]

Heiney, III et al.

[11] 4,228,675
[45] Oct. 21, 1980

[54] EXHAUST GAS SENSOR ELECTRICAL CIRCUIT IMPROVEMENT

[75] Inventors: Elmer T. Heiney, III, Huntington Woods; Stanley R. Merchant, Garden City, both of Mich.

[73] Assignee: Ford Motor Company, Dearborn, Mich.

[21] Appl. No.: 5,422

[22] Filed: Jan. 22, 1979

[51] Int. Cl.$^3$ ............................................. G01N 27/12
[52] U.S. Cl. ................................................................ 73/23
[58] Field of Search .................... 73/23, 27 R; 422/98

[56] References Cited

U.S. PATENT DOCUMENTS

| | | | |
|---|---|---|---|
| 3,868,846 | 3/1975 | Kushida et al. | 73/27 R |
| 3,886,785 | 6/1975 | Stadler et al. | 73/27 R |
| 3,932,246 | 1/1976 | Stadler et al. | 73/27 R |
| 4,151,503 | 4/1979 | Cermak et al. | 73/27 R |

*Primary Examiner*—Stephen A. Kreitman
*Attorney, Agent, or Firm*—Robert W. Brown; Clifford L. Sadler

[57] ABSTRACT

An exhaust gas sensor electrical circuit is improved by the provision of circuit means for inhibiting reduction in the magnitude of the change in voltage signal produced in the sensor circuitry. The reduction in magnitude change would otherwise result from prolonged exposure of the sensor ceramic elements to exhaust gases produced by combustion of a rich air/fuel mixture or a lean air/fuel mixture. The sensor has a titania or other exhaust gas sensing element responsive to temperature and to the partial pressure of oxygen. A second metal oxide ceramic element also is responsive to exhaust gas sensor temperature, but is more slowly responsive to the partial pressure of oxygen in the exhaust gases. Prolonged exposure of the second element in the sensor to rich-mixture exhaust gases or to lean-mixture exhaust gases can lead to a temporary but substantial loss of output signal magnitude from the sensor in the absence of the inhibiting means of the improved circuitry.

10 Claims, 7 Drawing Figures

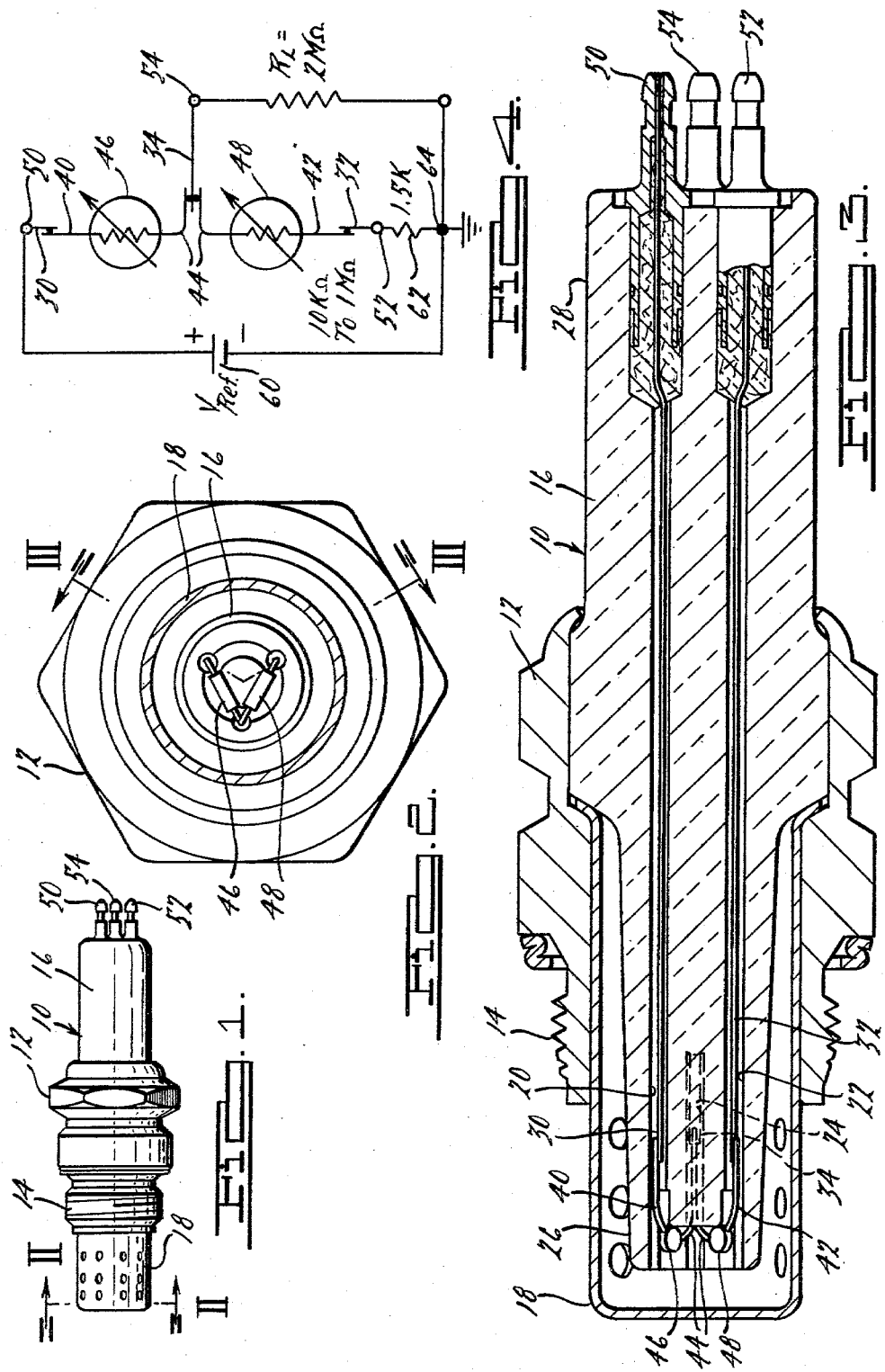

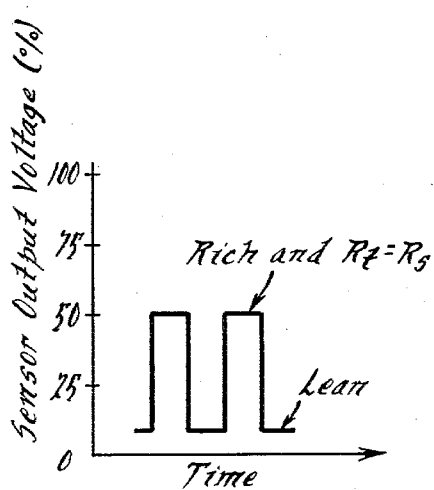
(a) Without Series Resistor 62 and at 850°C
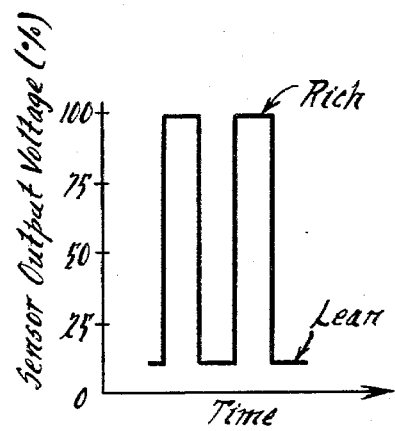
(b) With Series Resistor 62 and at 850°C
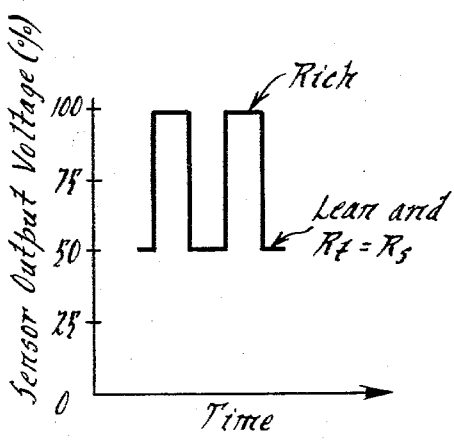
(c) Without Shunt Resistance $R_L$ ($R_L = \infty$) and at 350°C
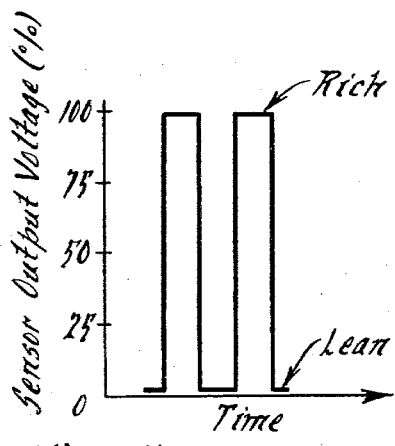
(d) With $R_L = 2M\Omega$ and at 350°C
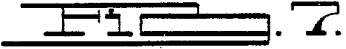
FIG. 7.

EXHAUST GAS SENSOR ELECTRICAL CIRCUIT IMPROVEMENT

BACKGROUND

This invention relates to an improved exhaust gas sensor electrical circuit. More particularly, the invention relates to circuitry suitable for use with an exhaust gas oxygen sensor of the type employing first and second metal oxide ceramic elements one of which is more responsive to the partial pressure of oxygen in the exhaust stream from an internal combustion engine than is the other of the metal oxide ceramic elements.

In a known type of exhaust gas oxygen sensor and associated electrical circuit, two metal oxide ceramic elements are electrically connected in series across a DC source of electrical energy. Both of the metal oxide ceramic elements are responsive to variations in their temperature. The temperature response is in the form of a variation in the electrical resistance between spaced lead wires that are embedded in or otherwise connected to the metal oxide ceramic materials. The electrical resistance between the lead wires also varies, to different degrees, as a function of the partial pressure of oxygen in exhaust gases to which the two metal oxide ceramic elements are exposed. These exhaust gases are produced by the combustion of an air/fuel mixture that may, in a feedback fuel control system, be caused to vary from rich to lean and from lean to rich with respect ot the stoichiometric level.

The response to the metal oxide ceramic elements to temperature and to the partial pressure of oxygen in the exhaust gases occurs over a normal temperature operating range that extends from about 350° C. to about 850° C. and which, in some cases, may extend from a lower temperature of 300° C. or less to a temperature as high as about 900° C. The preferred form of the exhaust gas oxygen sensor utilizes an oxygen sensing element that is quite porous and is made from titania, a metal oxide ceramic material responsive to both partial pressure of oxygen and to temperature with a resistance which decreases substantially as its temperature increases. The resistance also decreases substantially as a result of a change from exposure to exhaust gases produced from combustion of a lean air/fuel mixture. A change from rich to lean produces the opposite variation in resistance, that is, a substantial increase.

The second ceramic element in the exhaust gas sensor may also be made from titania material, but preferably is more dense than the oxygen-sensing titania element to lengthen the time rate of response to the second element to variations in the partial pressure of oxygen as compared to the oxygen sensing element. Otherwise stated, the oxygen sensing element should respond quickly to variations in oxygen content of exhaust gases and the second element should respond more slowly, i.e., have a lengthened time rate of response thereto. The response of the second element, usually referred to as a thermistor element, to variations in its temperature preferably is substantially similar to the response of the oxygen-sensing element.

The output signal from the exhaust gas oxygen sensor is a voltage measured between the junction formed between the first and second metal oxide ceramic elements and one of the leads of the DC source of electrical energy. When the air/fuel ratio of the mixture supplied to the internal combustion engine is switched cyclically from rich to lean and from lean to rich typically with a frequency approximately one Hz, then the output voltage signal varies from almost 100% of the source voltage to nearly 0% of this voltage and then back to 100% thereof at a frequency corresponding to that of the variation in the air/fuel ratio. This variation in voltage magnitude is substantially independent of temperature due to the presence of the second metal oxide ceramic element which, as compared to the first element, has little time rate of change of electrical resistance as a function of the variation in partial pressure of oxygen in the exhaust gases.

SUMMARY OF THE INVENTION

The second metal oxide ceramic element or thermistor used in the above-described exhaust gas sensor for purposes of temperature compensation does have some response to the partial pressure of oxygen in exhaust gases to which it is exposed. Because the second element has a much slower time rate of response to variations in oxygen partial pressure than does the first element, a desirable sensor output signal generally is obtained. It has been found, however, that upon prolonged exposure of the second metal oxide ceramic element to exhaust gases produced by the combustion of a rich mixture, the electrical resistance between the lead wires in the second metal oxide ceramic element becomes more and more equal to the electrical resistance of the first metal oxide ceramic element. This is particularly pronounced in the upper portion of the sensor temperature range extending between 350° C. and 850° C. Similarly, in the lower portion of this temperature range, the electrical resistance of the second metal oxide element tends to approach the resistance of the first metal oxide element when the second element is exposed to exhaust gases produced by the combustion of a lean air/fuel mixture for a prolonged period of time. In either case, the term "prolonged period of time", means a time period of perhaps several minutes or more. This time period is prolonged in the sense that it is much greater than the usual time period during which the sensor metal oxide elements would be continuously exposed to exhaust gases produced by either rich or lean-mixture compositions.

In accordance with the improvement of the invention, the first and second metal oxide elements described above are utilized in combination with a source of electrical energy. Circuit means connect the first and second elements to the source of electrical energy. Additional circuit means are provided for inhibiting reduction in the magnitude of the change in voltage, measured between one of the leads of the source of electrical energy and the junction formed between the first and second metal oxide elements, which reduction in voltage magnitude change would otherwise result from prolonged exposure of the second metal oxide element to exhaust gases produced by combustion of a rich air/fuel mixture prior to change to a lean air/fuel mixture or vice versa. In normal sensor operation with cyclical air/fuel variation, the invention also extends the operating temperature range of the oxygen sensor at both the upper and/or lower portions of the range.

The invention may be better understood by reference to the detailed description which follows and to the drawings:

BRIEF DESCRIPTION OF THE DRAWINGS

FIG. 1 is an elevational view of a titania exhaust gas oxygen sensor suitable for installation in the intake manifold of an internal combustion engine;

FIG. 2 is a sectional end view, taken along the line II—II in FIG. 1, and is shown in enlarged scale;

FIG. 3 is a sectional view, taken along the line III—III of FIG. 2, showing the internal structure of the sensor of FIGS. 1 and 2 also on an enlarged scale;

FIG. 4 is a circuit diagram illustrating the manner in which the titania oxygen sensing element and the thermistor shown in FIGS. 1 through 3 are electrically connected with circuitry designed to receive the sensor output voltage;

FIG. 7 consists of four graphs illustrating the voltage response of the titania exhaust gas oxygen sensor as a function of time, under varying lean/rich mixture conditions following exposure of the sensor metal oxide elements to rich [FIGS. 4(a) and 4(b)] and to lean [FIGS. 4(c) and 4(d)] mixture exhaust gases for prolonged periods; by lean/rich mixture conditions is meant exposure to exhaust gases produced with an air/fuel ratio that varies varies by about 0.1 ratios above and below stoichiometry.

DETAILED DESCRIPTION

Figure 5:
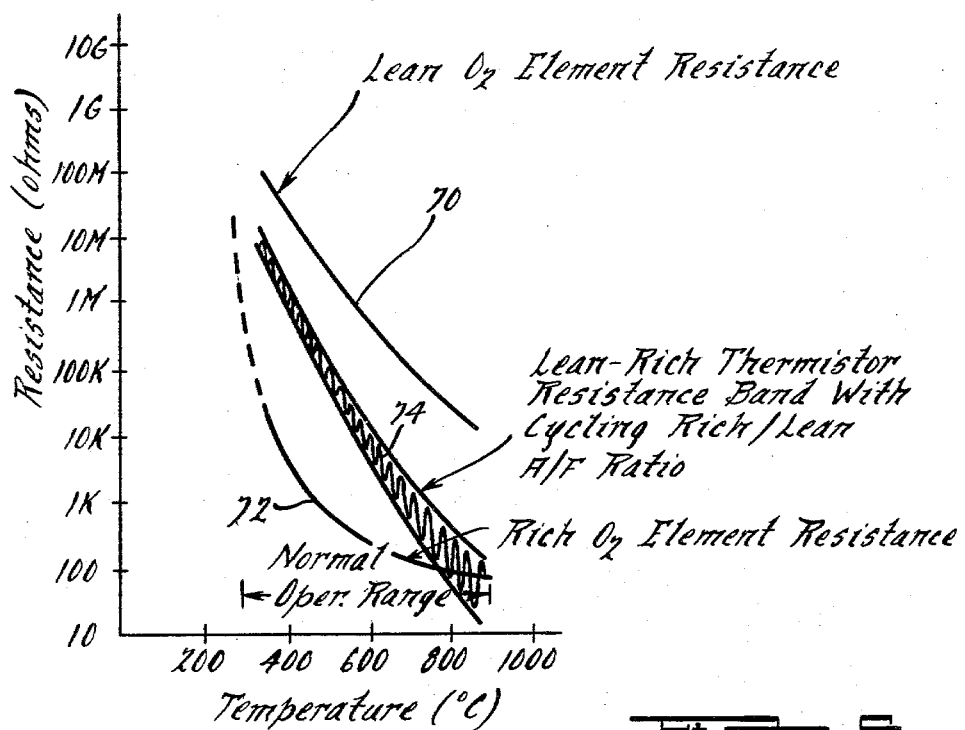
FIG. 5 is a graph of both the oxygen sensor element and thermistor element resistances as a function of temperature over the operating temperature range from about 300° C. to about 900° C.

With particular reference now to FIGS. 1 through 3, wherein like numerals refer to like parts in the several views, there is shown a complete titania exhaust gas sensor assembly generally designated by the numeral 10. The sensor 10 includes a steel body 12, which may be substantially identical to a typical spark plug body, having a threaded portion 14 for engagement with a suitably threaded aperture provided within the exhaust system of an internal combustion engine (not shown). In most cases, the sensor 10 would be installed in an aperture at a location in the exhaust manifold or conduit near the flange that would connect to an exhaust pipe. A ceramic insulator 16 extends through the body 12 and has a tapered portion 26 projecting outwardly from the body 12 into the volume defined by the boundaries of a perforated protection tube 18. There are three longitudinal passages 20, 22 and 24 extending from the projecting end 26 of the ceramic insulator to its opposite end 28. Wires 30, 32 and 34 are located in the respectively corresponding passages 20, 22 and 24 and are of a heat resistance character, preferably being made from an alloy such as 80% nickel-20% chromium wire. These electrically conductive wires are welded to previous-metal wire leads 40, 42, and 44, which are embedded in disc-shaped ceramic elements 46 and 48.

Element 46 is a ceramic titania $O_2$ sensor responsive to the partial pressure of oxygen in the gaseous medium to which this element is exposed. Sensor element 46 may be fabricated in accordance with the teachings of commonly assigned U.S. Pat. Nos. 3,886,785 issued June 3, 1975 and 3,932,246 issued Jan. 13, 1976, both in the names of Stadler et al. With regard to the fabrication of the oxygen sensing element 46, it is suggested that consideration be given to the teachings of commonly-assigned and previously or concurrently-filed patents, relating to exhaust gas ensors or thermistors, expected to issue subsequent to the filing date of this patent application.

The element 48 is a thermistor. The thermistor may be made from titania ceramic material of greater density than the density of the porous titania oxygen sensor 46. Alternatively, the thermistor 48 may be constructed in accordance with the teachings of copending and commonly-assigned U.S. patent application Ser. No. 857,498 filed Dec. 5, 1977, now U.S. Pat. No. 4,162,631, in the names of Logothetis, Laud and Park and entitled "Rare Earth-Yttrium, Transition Metal Oxide Thermistors". The thermistor 48 is intended to provide temperature compensation in accordance with the improved exhaust gas sensor electrical circuit illustrated in FIG. 4 and is intended to be substantially nonresponsive to variations in the partial pressure of oxygen in the gaseous medium to which it is exposed. Again, with respect to thermistor element fabrication, commonly-assigned and subsequently issued patents should be considered.

The sensor of FIGS. 1 through 3 is intended to be used in conjunction with electronic circuitry for closed-loop feeback control of the amount of fuel supplied to an internal combustion engine. The sensor indicates whether the exhaust gases contain a substantial amount of HC and CO or whether instead there is a substantial amount of $CO_2$, $H_2O$ and $O_2$, thereby indicating whether or not the air/fuel ratio of the mixture supplied to the engine was rich or lean with respect to the stoichiometric value of about 14.7 parts of air to each part of fuel by weight. This air/fuel ratio typically is expressed as a normalized air/fuel ratio lambda, wherein the actual ratio is divided by the stoichiometric value and the stoichiometric ratio therefore is represented as 1.0 in accordance with well known practice.

The exhaust gas sensor 10 has identical terminals 50, 52 and 54 designed for connection to external circuitry as specified above to enable it to be used in a feedback fuel control system. With particular reference now to FIG. 4, there is shown a circuit that schematically represents the manner in which the sensor 10 is utilized in association with such external circuitry. The exhaust gas sensor circuitry shown in FIG. 4 embodies the inventive improvement over the prior art circuitry illustrated and described in copending, commonly-assigned U.S. patent application Ser. No. 839,706 filed Oct. 10, 1977 and entitled "Thermistor Temperature Compensated Titania Exhaust Gas Sensor."

In FIG. 4, a DC source of regulated reference voltage 60 has its positive terminal connected to terminal 50 of the sensor oxygen responsive element 46. The lead wires 40, 42 and 44 from the sensor 46 and thermistor 48 are welded or otherwise joined, respectively, to lead wires 30, 32 and 34 to interconnect the two ceramic elements 46 and 48 as shown. The thermistor element 48 is connected through a response-shaping resistor 62 to ground potential at 64. The output voltage of the sensor 10 is taken between the sensor terminal 54 and ground potential. This signal is applied across the input impedance or load resistance $R_L$ (about two megohms) of the engine control electronic circuitry.

The input voltage to the circuit of FIG. 4 is obtained from the source reference 60 and is applied across the voltage divider comprising the series-connected variable resistances of oxygen sensor 46 and thermistor 48 in series with the response-shaping resistor 62. The output voltage of the improved exhaust gas sensor circuitry will be considered as being the voltage between the ground lead of the source of electrical energy 60 and the junction formed between the thermistor 48 and the oxygen sensing element 46. This is the voltage across the resistance $R_L$. This resistance is of considerable importance in accordance with the concept of the invention, as is resistor 62, which preferably has a positive temperature coefficient in contrast to the typical negative temperature coefficients of the metal oxide ceramic elements 46 and 48.

The resistance values of both the oxygen sensor 46 and the thermistor 48 vary as a function of temperature and in the same direction, that is, the resistance of these elements decreases with increasing temperature. As a result, the voltage dividing effect provides an output voltage across the load resistance $R_L$ that is substantially independent of temperature. The oxygen sensor 46, however, has a resistance which varies not only with temperature but also with the partial pressure of oxygen in the gaseous medium to which the sensor is exposed. An increase in the resistance of the oxygen sensor 46 causes the output voltage across the load $R_L$ to decrease, and a reduction in the resistance of the oxygen sensor causes a corresponding increase in the output voltage across the resistance $R_L$. Otherwise stated, an increase in oxygen content in the engine exhaust gases (lean, with respect to stoichiometry, air/fuel mixture supplied to the engine) surrounding the oxygen sensing device 46 causes its resistance to increase and thereby causes a reduction in the voltage across the load resistance $R_L$. A decrease in the oxygen content of the engine exhaust gases (rich air/fuel mixture supplied to the engine) causes the resistance of the oxygen sensor 46 to decrease in a corresponding manner and this causes an increase in the voltage across the load resistance $R_L$.

Titanium dioxide (titania) is a material that occurs naturally in mixture with other minerals. The titania is obtained by precipitation from a solution of minerals that include titania. When thus obtained by precipitation, the titania has an anatase crystal structure. When the titania material in this crystal structure is formed into an exhaust gas oxygen sensor, it is first thermally treated in a manner that allows the crystal structure to change from anatase to rutile. An increase in the temperature of the rutile material above room temperature induces oxygen vacancies into the crystal structure. This results in ionization of the titanium atoms interstitially located in the crystal structure. The concentration of the interstitial titanium ions and oxygen vacancies increase as temperature rises, and these variations in concentration are of considerable significance in the use of the titania as a sensor material. The titania oxygen sensor 46 is deliberately made considerably more porous than is the titania or other metal oxide thermistor 48. This considerably increases (slows down) the time rate of response of the thermistor 48 as compared to that of the oxygen sensing element 46. For this reason, cyclical air/fuel mixture variations from rich to lean and from lean to rich, with respect to stoichiometry, at the frequencies occurring in feedback fuel control systems for internal combustion engines, produce little variation in the thermistor response to the resulting exhaust gases.

The curve 70 in FIG. 5 represents the resistance of the metal oxide oxygen sensing element 46 when located in the exhaust gases emanating from an engine supplied with a lean mixture and the curve 72 when the engine is supplied with a rich mixture. Curve 74 illustrates the resistance of the thermistor 48 as a function of temperature. The curve 74 is of alternating character indicating the small variation of the thermistor resistance that occurs as the air/fuel ratio supplied to the engine oscillates back and forth about stoichiometry. From curve 74, it is quite evident that there is but very minor variation in the resistance of the thermistor 48 as a function of the oxygen content in the gaseous medium surrounding the sensor. This is much in contrast to the curves 70 and 72 representing, respectively, the lean and rich resistance values over the normal operating range of exhaust gas sensor 10. Of course, the actual resistance values for the oxygen sensing element 46 would vary back and forth between the curves 70 and 72 as the air/fuel ratio supplied to the engine was varied about stoichiometry. At the left side of the graph of FIG. 5, it may be seen that the curves 70 and 72 come together at low temperatures. This indicates that titania is not responsive to the surrounding oxygen concentration at low temperatures.

If it is assumed that a titania oxygen sensing element, such as sensor element 46, is located in an environment in which the oxygen concentration is constant and only the temperature varies, then the number of vacancies in the titania structure may change due to thermal energy. However, the titanium atom, in those titanium oxide molecules having but one oxygen atom, have only two of their four valence electrons covalently bonded with oxygen. As the temperature of the titania increases, the thermal energy supplied to the molecules in the structure increases and the oxygen vacancies therein have greater mobility. As the oxygen deficiency or concentration of Ti interstitials increases, more electrons become available for the conduction process, and the resistivity of the material decreases. The conductivity of the titania increases or, otherwise stated, its resistance decreases as a function of temperature, as is indicated in FIG. 5 for both the thermistor element 48 and oxygen sensor element 46.

If it is now assumed that a sensor element 46 of titania is positioned in an environment of varying oxygen partial pressure and that it is at a temperature within the titania operating range, for example, 600° C., then the number of vacancies in titania increases or decreases as a function of oxygen partial pressure.

If a titania oxygen sensor 46 is positioned in the exhaust stream of an internal combustion engine and if the air-fuel mixture supplied to such engine continually varies between lean and rich with respect to stoichiometry, the partial pressure of oxygen to which the sensor is exposed varies cyclically. When the mixture is lean, there is an excess of oxygen in the exhaust gas and few oxidizable carbon compounds. The titania element has a relatively high resistance, on the order of about 0.5 megohms. This is because oxygen from the exhaust gases will have been adsorbed on the surface of the titania element. The adsorbed oxygen atoms on the titania surface annihilate oxygen vacancies and interstitial titanium ions and migrate into the titania crystal structure. In an oxygen deficient oxide, both oxygen vacancies and interstitial ions may be involved in an equilibrium reaction with oxygen in the surrounding environment. In this equilibrium reaction, the partial pressure of oxygen in the environment determines whether the interstitial ions or the oxygen vacancies play the predominant role in the oxygen transfer process. In both cases, there is an acquisition of electrons followed by an annihilation of a vacancy. The electrons at low sensor operating temperatures are provided by charge transfer particles on the TiO$_2$, an electrical conductor having a "pool" of available electrons. At higher temperatures, thermal energy is sufficient to provide electrons required at the titania surface for the process of vacancy annihilation.

The lower the number of vacancies in the titania crystal structure, the higher is its electrical resistance. On the other hand, the more vacancies that are created in the crystal structure, the lower is the titania resistance.

When the exhaust gases change from lean-to-rich (L-R), a percentage of the oxygen atoms in the titania structure are removed to create additional vacancies. The oxygen leaves the titania crystal structure probably as a negatively charged ion. As a result, there is a positively charged vacancy left behind. At the titania surface, either the oxygen ion reacts with an oxidizable carbon compound in the exhaust gas or two oxygen atoms or ions unite to form an oxygen atom.

When the exhaust gases change to a composition corresponding to a lean mixture, the concentration of oxidizable carbon compounds is drastically reduced and an excess of oxygen appears in the exhaust gas. The oxygen concentration gradient reverses, and oxygen atoms are adsorbed on the titania surface and fill vacancies therein as was previously mentioned.

Figure 6:
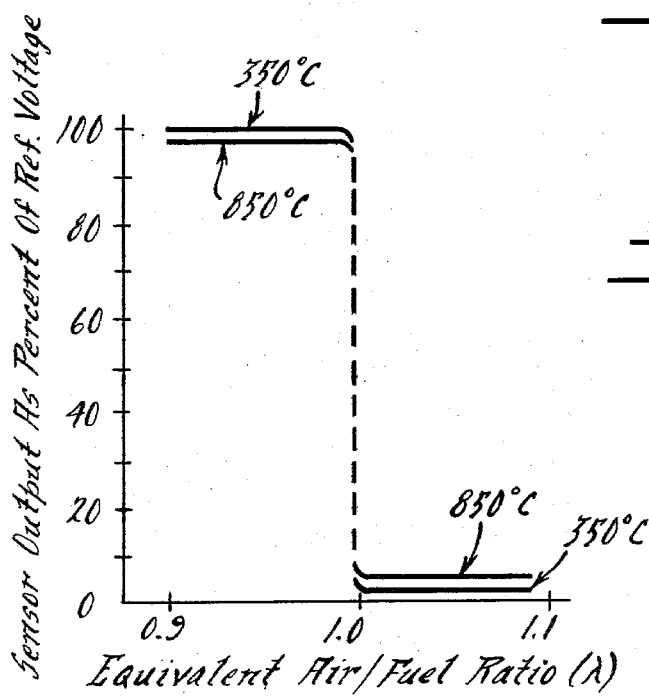
FIG. 6 is a graph of sensor output voltage as a percent of the input (reference) voltage versus equivalent air/fuel ratio.

FIG. 6 illustrates the manner in which the output voltage of the sensor 10, connected in the circuit of FIG. 4, varies as a function of air-fuel ratio where this ratio changes from rich (below 14.7) to lean (above 14.7). When the mixture is rich, the sensor oxygen responsive metal oxide element 46 has a low resistance and the sensor output voltage is almost 100 percent, the percentage figure being the ratio of the actual output voltage to the input reference voltage multiplied by 100 percent. It may be seen that, with the temperature compensation provided by the thermistor metal oxide element 48, there is very little variation in the sensor output voltage as a function of variation in temperature between 350° C. and 850° C. Under rich conditions, the removal of oxygen from the titania structure to create new vacancies provides additional electrons from the titania atoms that may be used for the purpose of conduction. This explains the greatly increased conductivity of titania when exposed to exhaust gases produced by the combustion of rich mixtures. The opposite effect explains the very high resistance and low conductivity of the titania sensor element when exposed to exhaust gases produced by lean mixtures.

In the preferred form of the invention, the oxygen sensing element 46 is manufactured in accordance with the teachings of concurrently filed and commonly assigned U.S. patent application Ser. No. 5,425 filed in the names of A. Achari and one of the present inventors and entitled "Improved Ceramic Element Sensor". Metal oxide ceramic elements manufactured according to the teachings of the above-mentioned patent application may have very rapid response times with respect to variation of their electrical characteristics resulting from changes in the partial pressure of oxygen in the gaseous medium to which the ceramic elements are exposed. One of these metal oxide elements is electrically connected in circuit with the other or second metal oxide ceramic element 48. The second element 48 provides temperature and other compensation in the circuit. The thermistor 48 may be manufactured in accordance with the teachings of concurrently-filed and commonly-assigned U.S. patent application Ser. No. 5,426 filed in the names of E. L. Heiney, one of the present inventors, S. R. Merchant and W. L. Green. This patent application is entitled "Exhaust Gas Sensor Having Two Titania Ceramic Elements". A thermistor constructed in accordance with the teachings of this last-mentioned patent application has a response time to variations of partial pressure of oxygen in the gaseous medium to which it is exposed that are much slower than those of the preferred oxygen sensing element 46.

In summary, the thermistor 48 is the second metal oxide element in the circuit of FIG. 4 and has an electrical resistance that varies as a function of the second element temperature substantially identically electrically to the temperature variation of the metal oxide oxygen sensing element 46, the first element in the circuit. The second element also has a substantially lengthened time rate of response to variations in the partial pressure of oxygen in the exhaust gases from an engine supplied with an air/fuel mixture switched from rich to lean and vice versa.

The thermistor 48 resistance values plotted in FIG. 5 are shown to vary within a narrow band over the operating range of the exhaust gas sensor 10 when the air/fuel ratio of the mixture supplied to the engine in which the sensor is located varies cyclically between rich and lean conditions. Should the air/fuel mixture remain either rich or lean for a long period as compared to the rate of the cyclical variation, then the tendency of the thermistor 48 is to have its electrical resistance vary such that it approaches the resistance of the oxygen sensing element 46 for the temperature and rich or lean air/fuel mixture condition existing at the time.

An analysis of the circuitry illustrated in FIG. 4 will establish that, in the higher temperature portion of the sensor operating temperature range, the series-connected response-shaping resistor 62 has a voltage limiting function. It constitutes circuit means for inhibiting reduction in the magnitude of the change in voltage, measured between one of the leads of the source of electrical energy 60 and the junction between the elements 46 and 48. This reduction in voltage magnitude change would otherwise result from prolonged exposure of the thermistor element 48 to exhaust gases produced by combustion of a rich air/fuel mixture prior to changing to a lean air/fuel mixture. If the thermistor element 48 is in a gaseous medium produced by combustion of a rich mixture for a prolonged period of time, the thermistor element 48 when at the higher portion of the operating temperature range will have a resistance that will tend to approach the resistance of the oxygen sensing element 46, which resistance may be substantially less than 1 kilohm and in fact may be on the order of 100 ohms or less. In such case, the resistor 62 becomes the highest resistance in the series circuit connected across the source of electrical energy; this series circuit comprises the oxygen sensing element 46; the thermistor 48 and the external resistor 62. The presence of the resistor 62 under these circumstances prevents the reduction in voltage magnitude described above as is illustrated in FIG. 7.

In FIG. 7, there are shown four graphs that depict the exhaust gas sensor 10 output voltage, measured across the resistance $R_L$, and expressed as a percent of the reference voltage, the input source of electrical energy. FIG. 7(a) depicts the sensor output voltage when the sensor is positioned in an exhaust gas medium produced by combustion of an air/fuel mixture cycling between rich and lean, the oxygen sensing and thermistor elements being at 850° C. and the thermistor element 48 previously having been exposed to the exhaust gases produced by a combustion of a rich mixture over a prolonged period of time. In the graph of FIG. 7(a), rich voltage amplitude is seen to be only about 50% of the input or supply voltage in the situation where the series-resistor 62 is absent (equal to zero ohms). It is assumed that the thermistor resistance $R_t$ has become equal to the resistance of $R_S$ of the oxygen sensing element 46 as a result of the prolonged exposure to rich-mixture exhaust gases.

FIG. 7(b) assumes the same conditions prevail as was stated in connection with FIG. 7(a), except that the series-connected resistor 62 is assumed to be present and to have a value of 1.5 kilohms. In this case, even through the resistance $R_t$ is assumed to equal the resistance $R_S$, the rich-mixture sensor output voltage is seen to be very nearly 100% of the input voltage, the desired result. This output response shown in FIG. 7(b) prevails throughout the sensor operating range with but slight variation in the output voltage at the lean-mixture condition.

FIG. 7(c) depicts the sensor output voltage as a function of time where the sensor is assumed to be at an operating temperature of 350° C., where the shunt resistance $R_L$ is assumed to be absent ($R_L$=infinity) and where it is assumed that the sensor has been subjected for a prolonged period of time to the exhaust gases produced by combustion of a lean mixture after which the air/fuel mixture producing the exhaust gases is cycled between rich and lean as indicated. It may be seen that under the rich-mixture condition, the sensor output voltage is equal to nearly 100% of the input voltage but that under lean air/fuel mixture conditions the voltage is only about 50% because the thermistor resistance $R_t$ has come to equal the lean-condition oxygen sensing element resistance $R_S$.

FIG. 7(d) illustrates the result which is achieved under the circumstances stated above in connection with FIG. 7(c), but where the resistance $R_L$ is present and equal to two megohms. Under this circumstances, it may be seen that the sensor output voltage remains at 100% under the rich-mixture condition and is very nearly equal to zero percent under the lean condition, the desired result.

The circuitry of the invention may be analyzed by considering the equation applicable to the calculation of the sensor output voltage ratio where V is the actual output voltage and $V_{Ref}$ is the applied input voltage, the output being expressed as the ratio therebetween:

$$V/V_{Ref} = \frac{R_L(R_t + R_{62})}{R_S(R_L + R_t + R_{62}) + R_L(R_t + R_{62})}$$

The thermistor 48 is a metal oxide element that has been described as having a different response to the partial pressure of oxygen depending upon the length of time of its exposure to exhaust gases produced by the combustion of a rich or lean air/fuel mixture. This length of time varies depending upon the operating temperature of the thermistor and upon its characteristics. If the thermistor is very dense, approaching its theoretical density, it will have very little response to changes in the composition of the exhaust gases to which it is exposed. On the other hand, a more porous thermistor will have a greater or more rapid rate of response to variations in the partial pressure of oxygen. In any event, the thermistor 48 operating in the circuit of FIG. 4 must have a slower rate of response to variation in the partial pressure of oxygen than does the oxygen sensing element 46 when the feedback fuel control system in which the oxygen sensor is used is causing the air/fuel mixture to oscillate between rich and lean conditions.

The series resistor 62 and the parallel resistor $R_L$ in the circuit of FIG. 4 are not necessary for the desired function of the circuitry under normal circumstances. However, there is a possibility that the fuel control system, either during its normal use in control modes that are open-loop or during abnormal operation, may cause the air/fuel mixture to be lean or rich for relatively long periods of time. The greater the duration of these periods of time, the more likely it is that either the series resistor 62 or the shunt $R_L$ resistance will be required for proper circuit operation to prevent the occurrence of a signal that would be improperly interpreted by electronic circuitry normally utilized in connection with the exhaust gas oxygen sensor 10.

The resistance $R_L$ advantageously may be the input impedance of the electronic circuitry mentioned above. Two megohms have been found to be a satisfactory input impedance value, but other resistances may be used as may be appropriate in a particular exhaust gas sensor application. Similarly, the value of the series resistor 62 may be other than that specified herein.

Based upon the foregoing description of the invention, what is claimed is:

1. An improved exhaust gas sensor electrical circuit employing a sensor of the type having a first negative-temperature-coefficient variably resistive element adapted to produce an electrical resistance change, as a function of the composition of the exhaust gases produced by the combustion of a rich or lean (with respect to stoichiometry) air/fuel mixture supplied to an internal combustion engine, in a circuit including a second negative-temperature-coefficient variably resistive element that is connected in series with the first variably resistive element, the improved exhaust gas sensor electrical circuit comprising:

the first element being formed from metal oxide ceramic material having spaced first and second electrical leads connected thereto, the metal oxide material having between the leads connected thereto an electrical resistance that varies both as a function of the temperature of the metal oxide material and as a function of the partial pressure of oxygen in the exhaust gases to which the metal oxide material is exposed;

the second element being formed from metal oxide ceramic material having, as compared to the metal oxide material of the first element, a longer time rate of response to variations in the partial pressure of oxygen in the exhaust gases from an internal combustion engine supplied with an air/fuel mixture changed from rich to lean and vice versa, the second element having spaced first and second electrical leads connected thereto, the second electrical lead of the first element having a junction formed with the first electrical lead of the second element;

a source of electrical energy having first and second electrical leads;

circuit means for connecting the first and second elements in a series-circuit between the first and second electrical leads of the source of electrical energy; and circuit means for inhibiting reduction in the magnitude of the change in voltage, measured between one of the leads of the source of electrical energy and the junction between the first and second elements, which magnitude change would otherwise result from prolonged exposure of at least the second element to exhaust gases produced by combustion of a rich air/fuel mixture prior to change to a lean air/fuel mixture or vice versa.

2. An improved exhaust gas sensor electrical circuit according to claim 1 wherein the electrical resistance variation of the first and second elements occurs at temperatures thereof from about 350° C. to about 850° C.

3. An improved exhaust gas sensor electrical circuit according to claim 2 wherein the magnitude change in voltage which would otherwise result tends to occur in the high temperature portion of the range from 350° C. to about 850° C.

4. An improved exhaust gas sensor electrical circuit according to claim 2 wherein the magnitude change in voltage which would otherwise result tends to occur in the low temperature portion of the range from 350° C. to about 850° C.

5. An improved exhaust gas sensor electrical circuit according to claims 1 or 2 wherein the inhibiting circuit means is a resistor.

6. An improved exhaust gas sensor electrical circuit in accordance with claims 1, 2 or 3 wherein the inhibiting circuit means is a resistor connected in series with the first and second elements in a circuit location between the second lead of the source of electrical energy and the junction formed between the first and second elements.

7. An improved exhaust gas sensor electrical circuit according to claims 1, 2 or 4 wherein the inhibiting circuit means is a resistor connected in parallel or shunt circuit with the second element and in a circuit location between the second lead of the source of electrical energy and the junction formed between the first and second elements.

8. An improved exhaust gas sensor electrical circuit according to claim 2 wherein the first and second elements have large electrical resistances when exposed to exhaust gases produced by the combustion of an air/fuel mixture that is lean because the lean-mixture exhaust gases contain an excess of oxygen and that have electrical resistances substantially reduced therefrom when exposed to exhaust gases produced by the combustion of an air/fuel mixture that is rich because the rich-mixture exhaust gases lack sufficient oxygen for complete combustion of the fuel, and wherein the inhibiting circuit means is a resistor.

9. An improved exhaust gas sensor electrical circuit according to claim 8 wherein the resistor is connected in series circuit with the first and second elements and is the largest resistance in the circuit when the first and second elements are at temperatures in the upper portion of the temperature range from about 350° C. to 850° C. and at least the second element has been exposed to rich exhaust gases for a prolonged period of time.

10. An improved exhaust gas sensor electrical circuit according to claim 8 wherein the resistor is connected in parallel or shunt with the second element and the parallel or shunt electrical resistance combination is the lowest resistance in the circuit when the first and second elements are in the lower portion of the temperature range from about 350° C. to about 850° C. and wherein at least the second element has been exposed to lean-mixture exhaust gases for a prolonged period of time.

* * * * *